United States Patent [19]

Rebrovic

[11] Patent Number: 5,416,224

[45] Date of Patent: May 16, 1995

[54] PROCESS FOR CONVERTING α-ACYL-SUBSTITUTED LACTONES TO α-ALKYLIDENE-SUBSTITUTED LACTONES

[75] Inventor: Louis Rebrovic, Cincinnati, Ohio

[73] Assignee: Henkel Corporation, Ambler, Pa.

[21] Appl. No.: 626,664

[22] Filed: Dec. 12, 1990

Related U.S. Application Data

[63] Continuation-in-part of Ser. No. 315,110, Feb. 24, 1989, abandoned.

[51] Int. Cl.$^6$ ............... C07D 307/33; C07D 309/30
[52] U.S. Cl. ..................... 549/273; 549/295; 549/323
[58] Field of Search .......... 549/295, 323, 273

[56] References Cited

U.S. PATENT DOCUMENTS 3,993,771 11/1976 Uematsu et al. ............ 424/279
4,179,446 12/1979 Tumlinson, III et al. ....... 260/343.6

FOREIGN PATENT DOCUMENTS 61-57572 3/1986 Japan .

OTHER PUBLICATIONS

Tsuboi, et al., "Reaction of Aldehydes With 1,3-Dicarbonyl Compounds In The Presence of Potassium Carbonate. A Convenient Synthesis of α,β-Unsaturated Carbonyl Compounds Via Deacylation", *Chemistry Letters*, vol. 12, 1978, pp. 1325–1328.

Zimmer, et al., "Substituted γ-Lactones. I. Preparation of α-Substituted γ-Butyrolactones by Condensation of γ-Butyrolactone with Aldehydes. Hydrogenation of the Condensation Products", *J. Org. Chem.*, vol. 24, 1959, pp. 28–32.

Chemical Abstracts, 135970x, vol. 78, No. 21, May 28, 1973, p. 354.

Tetrahedron Letters, vol. 39, 1978, pp. 3753–3756; Y. Ueno, et al.; "Deacylative Condensation I".

Journal of Organic Chemistry, vol. 42, No. 7, 1977, pp. 1180–1185; G. M. Ksander et al.; "A Method For The Synthesis Of Unsaturated Carbonyl Compounds".

JACS, vol. 74, 3120 (pp. 3122, 3123 and 3124), 1952 Taft, R.

"Mechanism and Theory in Organic Chemistry", 3rd edition, Lowry and Richardson, pp. 152 to 153, 1987.

*Primary Examiner*—Bernard Dentz
*Assistant Examiner*—Ba K. Trinh
*Attorney, Agent, or Firm*—Ernest G. Szoke; Wayne C. Jaeschke; Henry E. Millson, Jr.

[57] ABSTRACT

A convenient stereoselective process for the preparation of α-alkylidene-substituted-γ-butyrolactones and δ-valerolactones is provided. The process involves reacting an α-acyl lactone, an aldehyde, and an alkali metal hydroxide in an inert diluent at an elevated temperature while removing water.

48 Claims, No Drawings

PROCESS FOR CONVERTING α-ACYL-SUBSTITUTED LACTONES TO α-ALKYLIDENE-SUBSTITUTED LACTONES

CROSS REFERENCE TO RELATED APPLICATIONS

This application is a continuation-in-part of application Ser. No. 07/315,110, filed Feb. 24, 1989, now abandoned.

BACKGROUND OF THE INVENTION

1. Field of the Invention

The present invention is directed to an improved process for the preparation of α-alkylidene-substituted lactones, and the Z and E isomers thereof.

2. Description of the Prior Art

There has been considerable interest in the preparation of α-alkylidene lactones in view of the recognized biological activity of α-methylenated-γ- and δ-lactones. Synthetic routes to these products generally involve either (a) formation of the α-methylene or α-alkylidene lactone from acylic precursors containing all of the desired functional groups via a ring closure reaction; or (b) conversion of an existing group at the α-position on a preformed lactone ring to the corresponding α-methylene or α-alkylidene group. The present invention is directed to the latter type of reaction and, more specifically, relates to a process wherein the hydrogen and acetyl groups present in the α-position of a lactone ring are removed and replaced with an α-alkylidene moiety.

Numerous methods for the synthesis of α-methylene lactones are discussed in the review articles of P. A. Greico (Synthesis 1975, 67) and N. Petragnani et al. (Synthesis 1986, 157). None of the reactions described in either reference, however, deal with the preparation of α-alkylidene lactones. In fact, there is only one mention of the reaction of an acetyl group which is substituted at the s-position. Ueno et al (Tetrahedron Lett. 1978, 3753) describe the reaction of α-acetyl-γ-butyrolactone with paraformaldehyde, lithium diisopropylamide in tetrahydrofuran to produce α-methylene-γ-butyrolactone.

Ksander et al in (J. Org. Chem. 1977, 42, 1180) describe the preparation of α-alkylidene lactones by the reaction of ethyl oxalylbutyrolactones, with an aldehyde in the presence of aqueous sodium hydroxide. There is no suggestion by Ksander et al to the use of α-acyl-substituted lactones of any type for the reaction.

A multi-step synthesis which involves formulating γ-lactone using sodium hydride and ethyl formate and then condensing the resulting enolate with an aldehyde to obtain the corresponding α-methylene-γ-lactone is reported by Murray et al in J. Chem. Soc., Chem. Commun., 1984 at pp. 132–133.

Ono et al (J. Org. Chem. 1983, 48, 3678) report the conversion of an ester group which is substituted at the α-position on a γ-butyrolactone ring to an α-isopropylidene moiety. The complex multi-step process involves reaction of the carbanion of an α-carboethoxy-γ-butyrolactone and 2-chloro-2-nitropropane in the presence of a 150-watt tungsten lamp followed by the addition of sodium bromide and heat. In the only situation where Ono et al utilize a ring structure having an acetyl group in the α-position, namely, 2-acetylcyclopentanone, the corresponding α-isopropylidene cyclopentanone is not produced.

In view of the availability of α-acyl-substituted lactones, particularly α-acetyl-γ-butyrolactones, it would be highly useful if a process were available wherein the acyl group could be readily replaced by an alkylidene moiety. It would be even more advantageous if the reaction was facile and utilized readily available reactants. These and other advantages are realized with the process of the present invention which will be described in more detail to follow.

SUMMARY OF THE INVENTION

Other than in the operating examples, or where otherwise indicated, all numbers expressing quantities of ingredients or reaction conditions used herein are to be understood as modified in all instances by the term "about."

The present invention is directed to an improved process for the preparation of α-alkylidene-γ-butyrolactones, α-alkylidene-δ-valerolactones, and the geometric isomers of the foregoing. In general, the process involves reacting an α-acyl lactone, an aldehyde and an alkali metal hydroxide in an inert diluent at a temperature in the range of 50° C. to 150° C. while removing water of reaction. The reactants are preferably present in essentially equimolar quantities in order to maximize yield. The diluent preferably is one which forms an azeotrope with water wherein the azeotrope boils in the range of 50° C. to 95° C. The diluent is typically utilized at a volume ratio (diluent: total reactant charge) of 1:1 to 20:1. In one especially useful embodiment of the invention the α-acyl lactone and alkali metal hydroxide are combined and reacted prior to the addition of the aldehyde. When using this method the aldehyde is generally added after about 60% to 75% of the theoretical amount of water has been removed from the reaction mixture. α-Acyl lactones utilized in the process can contain one or more hydrocarbon radicals having from 1 to 20 carbon atoms on the ring. The hydrocarbon radicals can be alkyl, cycloalkyl, aryl or substituted aryl groups. If more than one hydrocarbon substituent is present, the total number of carbon atoms of the combined substituents typically does not exceed about 20. Acetyl is a preferred acyl moiety. The aldehydes will correspond to the formula R'CHO where R' is an alkyl, alkenyl, cycloalkyl or cycloalkenyl radical having from 1 to 20 carbon atoms and the alkali metal hydroxide can be sodium hydroxide, which is preferred, potassium hydroxide or lithium hydroxide. Benzene, toluene, xylene and cyclohexane are particularly useful diluents for conducting the reaction.

DETAILED DESCRIPTION

The present invention relates to a process for converting α-acyl-substituted lactones to α-alkylidene-substituted lactones. The α-alkylidene substituents include n-alkylidenes, cycloalkyl-substituted alkylidenes, and similar groups. α-Alkylidene substituted α-butyrolactones are also referred to herein as 3-alkylidenedihydro-2(3H)-furanones. This latter nomenclature is particularly useful when designating compounds which have multiple substituents on the ring and is employed throughout the examples.

The reaction involves reacting an α-acyl lactone, an aldehyde and an alkali metal hydroxide. The reaction is typically carried out in an inert diluent medium. The process is adaptable for use with any 5- or 6-membered lactone having an acyl moiety substituted at the α-position on the ring. The other ring positions can be unsubstituted or substituted with one or more hydrocarbon groups. α-Acyl lactones useful in the process will correspond to the general formulae

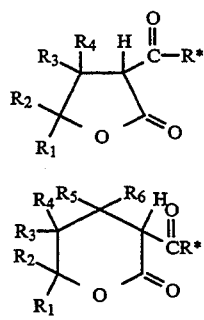

(I)

(II)

wherein R* is a $C_{1-8}$ alkyl group and $R_1$, $R_2$, $R_3$, $R_4$, $R_5$ and $R_6$ are, independently, selected from the group consisting of hydrogen or a hydrocarbon radical having from 1 to 20 carbon atoms. The hydrocarbon radicals can be alkyl, cycloalkyl, aryl or substituted-aryl groups. Generally, when more than one hydrocarbon group is present on the lactone ring the total number of carbon atoms of the combined hydrocarbon substituents will not exceed twenty (20). Particularly useful hydrocarbon radicals include $C_{1-8}$ alkyl, $C_{3-6}$ cycloalkyl, phenyl, $C_{1-8}$ alkyl-substituted phenyl, benzyl and $C_{1-8}$ alkyl-substituted benzyl.

In one especially useful embodiment of the invention, the lactone corresponds to formula I, R* is $C_{1-4}$ alkyl and $R_1$, $R_2$, $R_3$ and $R_4$ are hydrogen or $C_{1-8}$ alkyl. In an even more preferred embodiment, R* is methyl, $R_1$ is $C_{1-8}$ alkyl and $R_2$, $R_3$, and $R_4$ are hydrogen.

In another especially useful embodiment, the lactone corresponds to formula II, R* is $C_{1-4}$ alkyl and $R_1$, $R_2$, $R_3$, $R_4$, $R_5$ and $R_6$ are hydrogen or $C_{1-8}$ alkyl. In an even more preferred embodiment, R* is methyl, $R_1$ is $C_{1-8}$ alkyl and $R_2$, $R_3$, $R_4$, $R_5$ and $R_6$ are hydrogen.

Aldehydes employed in the process correspond to the general formula R'CHO where R' is an alkyl, alkenyl, cycloalkyl or cycloalkenyl radical having from about 1 to 20 carbon atoms.

The choice of aldehyde will dictate the nature of the α-alkylidene substituent. For example, when the α-acyl lactone corresponds to formula I, the resulting α-alkylidene-γ-butyrolactone will have the formula

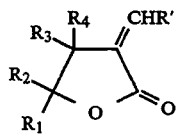

(III)

where $R_1$, $R_2$, $R_3$, $R_4$ and R' are the same as previously defined. When the α-acyl lactone corresponds to formula II, the resulting α-alkylidene-δ-valerolactone has the formula

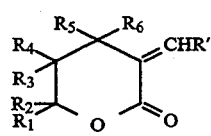

(IV)

where $R_1$, $R_2$, $R_3$, $R_4$, $R_5$ and $R_6$ and R' are the same as previously defined. In a particularly useful embodiment of the invention, the R' radical of the aldehyde and of the corresponding α-alkylidene lactone is a $C_{1-8}$ alkyl or alkenyl, or a $C_{3-8}$ cycloalkyl or cycloalkenyl radical.

The reaction is stereoselective for the Z isomer when the R' group of the aldehyde has a Taft Steric Substituent constant (abbreviated Es) equal to or less than −0.79. That is, the Z isomer is formed in a greater amount than the E isomer. A value less than -0.79 means that the value is more negative than -0.79.

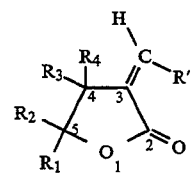

(Z)-isomer

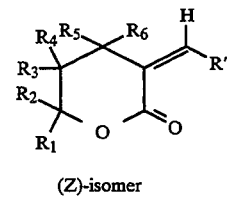

(Z)-isomer

Where the R' group of the aldehyde has a Taft Steric Substituent constant greater than −0.79, the reaction is stereoselective for the E isomer. That is, the E isomer is formed in a greater amount than the Z isomer.

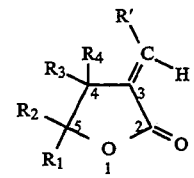

(E)-isomer

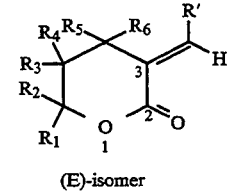

(E)-isomer

Table 1 shows the weight percent of the E and Z isomers in the product mixture for the synthesis of the substituted dihydro-2-(3H)-furanones listed using the process of the invention.

TABLE 1

| DIHYDRO-2(3H)-FURANONE | $Es^1$ | % E | % Z |
|---|---|---|---|
| 3-1-methylpropylmethylene-5-ethyl | −1.13 | 32 | 68 |
| 3-cyclohexylmethylene-5-methyl | −0.79 | 32 | 68 |
| 3-hexylidene-5-ethyl | −0.45 | 60 | 40 |
| 3-phenylmethylene-5-butyl | −2.55 | 100 | 0 |
| 3-phenylmethylene | −2.55 | 100 | 0 |
| 3-hexylidene-5-methyl | −0.45 | 55 | 45 |

1-Taft Steric Substituent Constant

An alkali metal hydroxide is necessarily utilized with the α-acyl lactone and aldehyde for the reaction. Suitable alkali metal hydroxides include sodium hydroxide, potassium hydroxide and lithium hydroxide. The alkali metal hydroxide can be used as such or added as an aqueous solution. While it is not necessary to add water with the reactants, the presence of some water in the reaction mixture is generally considered to be advantageous. Since the alkali metal hydroxides are hygroscopic, there is generally sufficient water associated with these materials for the reaction. Also, as the reaction proceeds, additional water is produced. However, if the alkali metal hydroxide is added as an aqueous solution, the amount of water used will be such that it will not exceed 50%, by volume, of the reaction mixture. More typically, if water is added it constitutes from about 1% to 25%, by volume, of the reaction mixture.

The reaction is carried out at a temperature in the range 50° C. to 150° C. using an inert diluent as the reaction medium. Any diluent which is a liquid under the conditions employed for the reaction and which is substantially inert under the reaction conditions can be employed. Illustrative diluents include benzene, toluene, xylene, pentane, hexane, heptane, octane, isooctane, cyclohexane, ethylbutyl ether, diethyl acetal, dipropyl acetal, dibutyl acetal and the like. Inert diluents which form an azeotrope with water are particularly advantageous. Inert diluents which form an azeotrope boiling in the range 50° C. to 95° C. are particularly useful. The volume ratio of diluent to reactants can range from about 1:1 to 20:1 but most generally ranges from 2:1 to 8:1. Benzene, toluene, xylene and cyclohexane are especially advantageous diluents for the reaction in view of their azeotroping ability and availability.

The manner of adding the reactants is not critical. All of the reactants can be combined at the outset of the reaction, or as is more generally the case, two of the reactants can be combined and the remaining reactant added continuously or incrementally. For example, the alkali metal hydroxide can be added to a mixture of the α-acyl lactone and aldehyde. In a particularly useful embodiment, the α-acyl lactone and alkali metal hydroxide are combined and at least partially reacted prior to addition of the aldehyde to the mixture. This prereaction is conveniently accomplished by refluxing the s-acetyl lactone and alkali metal hydroxide in a suitable diluent while removing water. The refluxing and azeotropic removal of water is typically carried out at a temperature in the range 50° C. to 95° C. When the distillation slows, usually when about 60% to 75% of the theoretical amount of water has been removed, the aldehyde is then added and the mixture is heated at reflux until essentially all of the water formed during the reaction is removed. As the water is removed, the temperature of the reaction increases to the maximum possible with the particular diluent being used. The temperature of the reaction mixture is generally maintained at about 75° C. to 125° C. during this stage of the reaction. If desired, the reaction temperature can be increased by distilling off the original diluent and adding a higher boiling inert solvent.

Essentially equimolar amounts of the reactants are preferably employed to optimize the yield of the α-alkylidene lactone. A slight molar excess, generally not exceeding 20% and, more preferably, less than 10% can be used for the lactone or the aldehyde and may be advantageous depending on the method of combining the reactants. For example, when the α-acyl lactone and alkali metal hydroxide are prereacted, a 10% to 15% molar excess of the aldehyde is often desirable.

All of the compounds of formulae III and IV as well as their isomers and mixtures of isomers in any proportions are useful as aroma chemicals in a variety of applications. A fragrance can be defined as a mixture of natural and/or synthetic materials which impart fragrance or aroma to another substance. Fragrances are used to impart odors to such substances as perfumes, colognes, and perfumed articles of all types such as cosmetics, room deodorizers, fabric softeners, laundry cleaning products, sanitary paper products, and candles just to name a few. Compounds that are used in fragrances include plant materials such as essential oils, flower oils, resins, animal secretions, isolates from plant materials, derivatives of plant materials, and aroma chemicals. The amount of fragrance used to impart odor to a substance varies. For example, perfume typically contains from about 15% to about 30% by weight of fragrance. Aroma chemicals are compounds which enhance or augment the characteristic odor of a fragrance. Aroma chemicals are single compounds with known structures as opposed to the other fragrance ingredients such as essential oils, flower oils, and animal secretions. Aroma chemicals are well known in the art of perfumery. Examples of aroma chemicals include but are not limited to benzyl acetate which exhibits a characteristic floral odor type, citronellol which exhibits characteristics rosy and citrus odor types, geraniol which exhibits characteristic floral, rose and geranium odor types, and isobornyl acetate which exhibits a characteristic pine needle odor type. When one or more aroma chemicals are added to a fragrance, a certain odor is enhanced or made more prominent. For example, U.S. Pat. No. 4,824,828 discloses the use of certain types of schiff bases in an aroma-enhancing process. Specifically, the inclusion of the schiff base of methyl anthranilate imparts a lemony undertone to a floral fragrance disclosed in Example X of the patent.

When the present compounds of formulas III and IV and the isomers and isomer mixtures thereof are incorporated into a fragrance, they enhance or augment the odor of those fragrances. For example, by itself, (E)-3-[2-(2,2,3-trimethylcyclopent-3-en-yl)ethenyl]dihydro-2(3H)-furanone has a floral aroma with tendencies toward oak character on dryout. It will be appreciated that the type of odor augmentation depends upon the nature of the fragrance and the amount of the compounds added. Typically, the amount of the compounds of the invention added to a fragrance will fall in the range of from about 0.01% to about 30% by weight. The preferred range is from about 0.5% to about 25% by weight. The mixtures of isomers generally obtained as the first product of the present process can be used as such and possess fragrances of their own in addition to their use as aroma chemicals. Moreover, each isomer possesses a distinct characteristic aroma, different from a mixture thereof, and different from its corresponding isomer.

The following examples illustrate the invention more fully but are not intended as a limitation on the scope thereof. In these examples all parts and percentages are given on a weight basis unless otherwise indicated.

EXAMPLE I

Preparation of α-Acetyl Lactone

Sodium hydroxide (100 g/400 g water) was charged to a one liter, four-neck flask equipped with an ice bath, mechanical stirrer, dry ice condenser, pot thermometer and addition funnel. Ethyl acetoacetate (325 g, 2.5 moles) and propylene oxide (174 g, 3.0 moles) were mixed and charged to the addition funnel. The pot was cooled to 15° C. and the ethyl acetoacetate-propylene oxide mixture was added below 20° C. over a period of two hours. The reaction mixture was then stirred for six hours and transferred to a separatory funnel and acidified with 225 ml of concentrated hydrochloric acid. The two layers were separated and the lower aqueous layer extracted three times with diethyl ether. The combined extracts were dried over sodium sulfate and the diethyl ether removed using a Rotovap at 70° C. (aspirator pressure). The resulting product was distilled using a packed column and a Perkins Triangle Head. Fractions 1–3 (94 g) contained mostly ethyl acetoacetate. A fourth fraction (170 g) boiling point at 112°–117° C. at 7 torr contained essentially 100% of the desired α-acetyl lactone, 3-acetyl-5-methyldihydro-2(3H)-furanone.

Conversion of the α-Acetyl Lactone to α-Alkylidene Lactone

3-Acetyl-5-methyldihydro-2(3H)-furanone (28.4 g; 0.200 mole) was combined with 200 ml toluene in a 500 ml flask fitted with a mechanical stirrer, a Dean-Stark trap and an addition funnel. Eight grams (0.200 mole) of sodium hydroxide was added and the mixture stirred at room temperature for 10 minutes and then heated under reflux for one hour during which time water was removed in the Dean-Stark trap. Cyclohexanecarboxaldehyde (25.7 g; 0.225 mole) was then slowly dripped into the reaction mixture over a period of approximately one hour. The mixture was heated under reflux for another four hours and the reaction mixture then cooled to room temperature and washed three times with 100 ml of $H_2O$ and dried over $Na_2SO_4$. Filtration followed by evaporation of the toluene solvent yielded 35 g of the crude α-alkylidene lactone product, composed of 48% Z-cyclohexylmethylene-5-methyldihydro-2(3H)-furanone and 24% E-cyclohexylmethylene-5-methyldihydro-2(3H)-furanone (GLC analysis).

The crude product was distilled under vacuum using a 1×20 cm Vigreaux column to obtain 20.8 g 3-cyclohexylmethylene-5-methyldihydro-2(3H)-furanone (94% assay by GLC, 50% yield, boiling range 105°–134° C. at 0.20 mm of Hg). The structure of the product was confirmed by proton and carbon nuclear magnetic resonance spectroscopy: $^1$HNMR (CDCL$_3$) δ6.57 (m, 0.37H), 6.0 (m, 0.63H), 4.6 (m, 1H) 3.44 (m,0.53), 3.1(m, 1H), 2.47 (m, 1H) 2.19 (m,0.47H), 1.87–0.9 (series of complex multiplets 13H). $^{13}$CNMR(CDCL$_3$) δ171.309, 170,148.981, 145.260, 124.788, 123.087, 73.990, 73.696, 39.393, 36.870, 35.766, 32.726, 32.550, 32.441, 31.515, 31.434, 25.869, 25.738, 25.396, 22.223, 21,775.

Isolation of (Z)-3-Cyclohexylmethylene-5-methyldihydro-2(3H)-furanone

A fractional distillation cut at 105° C. was isolated and found to contain 86% of the Z isomer and 7.8% of the E isomer (1.5 gms). This cut solidified on standing and was recrystallized from 7 ml of 50/50 methanol/water to give white crystalline Z isomer of 98% (GLC) purity. This product seemed to melt at 45.5° C., but then became a slush up to 53° C.

EXAMPLE II

To demonstrate the versatility of the process and the ability to obtain lactones having an n-alkylidene moiety in the α-position, Example I was repeated except that heptaldehyde was substituted for the cyclohexanecarboxaldehyde. Upon distillation of the reaction mixture, 3-heptylidene-5-methyldihydro-2(3H)-furanone was recovered in 54.5% yield (boiling range 113°–120° C. at 0.05 mm of Hg). The structure of the product was confirmed by proton nuclear magnetic resonance: $^1$HNMR (CDCL$_3$) 66.55 (M,0.66H), 6.04 (m, 0.34H), 4.6(m, 1H) 3.0–1.85 (series of complex multiplets, 4H) 1.44–1.0 (multiplet with triplet at 1.25, 11H), 0.75 (distorted triplet, 3H).

When the reaction was repeated using potassium hydroxide as the base, the reaction proceeded without difficulty although at a somewhat slower rate to produce 3-heptylidene-5-methyldihydro-2(3H)-furanone.

EXAMPLE III

Example I was repeated using heptaldehyde, 3-acetyl-5-ethyldihydro-2(3H)-furanone and sodium hydroxide to obtain the corresponding α-alkylidene-γ-butyrolactone. The product, 3-heptylidene-5-ethyldihydro-2(3H)-furanone, boiled in the range 113°–118° C. (0.06 mm/Hg) and had the following proton nuclear magnetic resonance spectrum: $^1$HNMR (CDCL$_3$) δ6.7(tt,0.42H), 6.2(tt, 0.58H), 4.42(M,1H) 3.1–0.8 (series of complex multiplets 20H)

EXAMPLE IV

To demonstrate the ability to prepare an α-methylene-γ-butyrolactone, 3-acetyl-5-butyldihydro-2(3H)-furanonewas reacted with sodium hydroxide and paraformaldehyde in accordance with the procedure of Example I.

3-Methylene-5-butyldihydro-2(3H)-furanone boiling at 87° C. (0.2 mm/Hg) was obtained in 70% yield. Proton and carbon nuclear magnetic resonance spectra for the product were as follows: $^1$HNMR (CDCl3 ) δ6.2 (very closely spaced triplet, 1H), 5.64 (very closely spaced triplet, 1H), 4.55 (pentet, 1H), 3.1 (m, 1H), 2.6 (m, 1H), 1.9–1.15 (m, 6H), 0.91 (t, 3H) $^{13}$CNMR (CDCl$_3$) δ170.368, 134.993, 121,712, 77.656, 35,979, 33,550, 26.999, 22,414, 13,919.

EXAMPLE V

3-Phenylmethylene-5-butyldihydro-2(3H)-furanone was prepared by reacting 3-acetyl-5-butylidihydro-2(3H)-furanone with sodium hydroxide and benzaldehyde in accordance with the procedure described in Example I. The crude product (64.5% yield) was recovered by distillation of the reaction mixture at 25°–147° C. (0.04 mm/Hg) to remove light ends. The structure was confirmed by proton nuclear magnetic resonance spectroscopy. $^1$HNMR (CDCl$_3$) δ7.5 (m,6H), 4.56 (pentet,1H),3.3 (ddd,1H) 2.8 (ddd,1H) 1.9–1.2 (m,6H), 0.86(t,3H)

The reaction was repeated using 3-acetyl-dihydro-2(3H)-furanone, sodium hydroxide and benzaldehyde to produce 3-phenyl methylene-dihydro-2(3H)-furanone. The crude yellow solid obtained from the reaction was recrystallized from chloroform to recover 3-phenylmethylene-dihydro-2(3H)-furanone, a yellow crystalline solid melting at 116° C. Proton and carbon nuclear magnetic resonance spectra for the product were as follows: $^1$HNMR (CDCl$_3$) δ7.526(t,1H, J=3 Hz), 7.45 (m,5H), 4.42(t,2H, J=7.6 Hz) 3.208 (dt, 2H, J=7.6, 3.0 Hz) $^{13}$CNMR (CDCl$_3$) δ172.455, 136.414, 134.598, 129.963, 129.805, 128.904, 123.685, 65.447, 27.368

EXAMPLES VI AND VII

Two reactions were carried out in accordance with the process of the invention using valeraldehyde. For one reaction (Example VI) 3-acetyl-dihydro-2(3H)-furanone was used and for the second reaction (Example VII) 3-acetyl-5-n-butyldihydro-2(3H)-furanone was employed. Both reactions used sodium hydroxide with toluene as the diluent and the reactants were present in essentially equimolar amounts. 3-Pentylidene-dihydro-2(3H)-furanone (86°–104° C. at 0.1 mm/Hg) and 3-pentylidene-5-n-butyldihydro-2(3H)-furanone (110°–131° C. at 0.01 mm/Hg) were obtained from the respective reactions. Proton nuclear magnetic resonance spectra for the products were as follows: 3-Pentylidene-dihydro-2(3H)-furanone: $^1$HNMR (CDCl$_3$) δ6.7 (m, 0.93H), 6.26 (m, 0.07H), 4.4 (t, 2H), 2.9 (m, 2H) 2.22 (m, 2H), 1.4 (m, 4H), 0.9 (t, 3H). 3-Pentylidene-5-n-butyldihydro-2(3H)-furanone: $^1$HNMR (CDCl$_3$) δ6.7 (tt, 0.4H), 6.2 (tt, 0.6H), 4.45 (m, 1H) 3.1–1.5 complex multiplets, 14H), 0.9 (two superimposed triplets, 6H).

EXAMPLE VIII

2-Methylbutyraldehyde was reacted with 3-acetyl-5-ethyldihyro-2(3H)-furanone and sodium hydroxide to produce 3-(1-methylpropyl)methylene-5-ethyldihydro-2(3H)-furanone (88% assay by GLC). The product boiled in the range 80°–94° C. at 0.2 mm of Hg and had the following proton nuclear magnetic resonance spectrum: $^1$HNMR (CDCl)$_3$ δ6.5(t d, 0.2 2H), 5.92(td,0.78H)$_3$ 4.4(m,1H),3.67–0.76 (series of complex multiplets, 16H)

EXAMPLE IX

To further demonstrate the versatility of the process and the ability to utilize a different diluent, the procedure of Example II was repeated. For this reaction, however, cyclohexane was employed as the diluent. After eight hours (total reaction time) the reaction was terminated and the crude product 3-heptylidene-5-methyldihydro-2(3H)-furanone was recovered in the usual manner (45.6% yield).

EXAMPLE X

Example I was repeated using propionaldehyde diethyl acetal as the azeotroping solvent for the reaction. For the reaction 100 ml propionaldehyde diethyl acetal was charged to the reactor with 14.9 g (0.10 mole) 3-acetyl-5-methyldihydro-2(3H)-furanone. The mixture was stirred and 4 g (0.10 mole) powdered sodium hydroxide added. The mixture was allowed to stir for 10 minutes and then heated to reflux for 5½ hours after which time 14.0 g (0.125 mole) cyclohexanecarboxaldehyde was added over a one-hour period. The mixture was heated under reflux for an additional twelve hours, cooled and worked up to recover 19 g crude 3-cyclohexylmethylene-5-methyldihydro-2(3H)-furanone (59% yield). The structure of the product was confirmed by proton and carbon nuclear magnetic resonance spectroscopy.

EXAMPLE XI p-Nitrobenzaldehyde was reacted with 3-acetyl-5-butyldihydro-2(3H)-furanone. For the reaction, 9.21 g (0.05 mole) of the furanone and 7.55 g (0.05 mole) of p-nitrobenzaldehyde were combined with 2.5 g (0.065 mole) of sodium hydroxide in 25 ml water and 25 ml ethanol. A reaction occurred immediately. The light yellow solid was recovered by filtration and washed with ethanol. The product, 3-(p-nitrophenyl)methylene-5-butyldihydro-2(3H)-furanone, was confirmed by carbon nuclear magnetic resonance spectroscopy. $^{13}$CNMR (CDCl$_3$) δ171.5, 148.0, 141.0, 133.8, 130.5, 130.0, 124.0, 178.1, 36.2, 34.0, 27.3, 22.4, 14.0.

EXAMPLE XIII

Preparation of (E)-3-(Phenylmethylene)-5-Butyldihydro-2(3H)-Furanone

To a mixture of 36.8 g (0.200 mole) of 3-acetyl-5-butyldihydro-2(3H)-furanone in 200 mL of toluene charged to a 500 mL flask fitted with a mechanical stirrer, Dean-Stark trap and an addition funnel was added 8.00 g (0.200 mole) of sodium hydroxide at once. The mixture was vigorously stirred for 10 mins. at room temperature and then heated under reflux for 1 hour while water was removed in the Dean-Stark trap. After the one hour period 23.9 g (0.225 mole) of benzaldehyde was added to the refluxing solution in 4–5 ml aliquats in 1 hour. The reaction was further heated under reflux for an additional 2.5 hours. The reaction mixture was then cooled to room temperature and washed with 3×80 ml of water. The water layer was extracted with 50 ml of toluene and the toluene layers combined. The toluene solution was then washed with 100 ml of saturated sodium chloride and dried over Na$_2$SO$_4$ and concentrated to 35.4 gms of an orange oil under rotoevaporation. 19.0 gms of this oil was subjected to simple straight takeover distillation (0.04 mm Hg: 25°–147° C.) to leave 16 g (64.5% yield) of (E)-3-(phenylmethylene)-5-butyldihydro-2 (3H)-furanone as a viscous liquid. $^1$HNMR (CDCl$_3$) δ7.5 (m, 6H), 4.56 (pentet, 1H), 3.3 (ddd, 1H), 2.8 (ddd, 1H), 1.9–1.2 (m, 6H), 0.86 (t, 3H).

EXAMPLE XIV

The process of Example 1 was carried out except that the aldehyde was 3,4-methylenedioxybenzaldehyde and the furanone did not contain a 5-methyl group to obtain (E)-3(3,4 methylenedioxyphenyl)methylene dihydro-3(3H)-furanone in substantially pure form. $^1$HNMR (CDCl$_3$) δ7.49(close spaced t, 1H), 7.1–6.85 (m, 3H), 6.04 (s, 2H), 4.47 (t, 2H), 3.21 (close spaced d of t, 2H) MP (CCl$_4$)–176° C.

EXAMPLE XV

The process of Example 1 was carried out except that the aldehyde was 3,4-methylenedioxybenyaldehyde to obtain (E)-3-(3,4-methylenedioxyphenyl)methylene-5-methyl-dihydro-2(3H)-furanone in substantially pure form. $^1$HNMR (CDCl$_3$) δ7.41(close spaced t, 1H), 7.06–6.76 (m, 3H), 6.00 (S, 2H), 4.75 (sextet, 1H), 3.32 (m, 1H), 2.74 (m, 1H), 1.48 (d, 3H).

EXAMPLE XVI

The process of Example 1 was carried out except that the aldehyde was 2-(2,2,3-trimethylcyclopent-3-en-yl) ethaldehyde and the furanone did not contain a 5-methyl group to obtain (E)-3-[2-(2,2,3-trimethylcyclopent-3-en-yl)ethenyl]dihydro-2 (3H)-furanone. $^1$HNMR (CDCl$_3$) [Redistilled E isomer] δ6.80 (m, 1H), 5.24 (close spaced m, 1H), 4.40 (t, 2H), 2.93 (m, 2H), 2.45–1.77 (m, 6H), 1.62 (close spaced m, 3H), 1.04 (s, 3H), 0.85 (s, 3H). BP 1.38°–156° C. at 0.20 mm Hg Yield 42–57%

EXAMPLE XVII

The process of Example I was carried out except that the aldehyde was 2-(2,2,3-trimethylcyclopent-3-en-yl)ethaldehyde to obtain 5-methyldihydro-3-[2,2,3-trimethylcyclopent-3-en-1-yl)ethenyl]2 (3H)-furanone. $^1$HNMR (CDCl$_3$) δ6.75 (m, 0.57H), 6.22 (m, 0.43H), 5.21 (close spaced m, 1H), 4.65 (m, 1H), 3.21–1.66 (m, 7H), 1.60 (close spaced m, 3H), 1.40 (t+, 3H), 1.0 (s, 3H), 0.73 (very close spaced d, 3H). BP 130°–145° C. at 0.30 mm Hg Yield 49–63%

EXAMPLE XVIII

The process of Example I was repeated except that the aldehyde was propionaldehyde and the furanone contained a 5-butyl group to obtain 3-propylene-5-butyldihydro-2(3H)-furanone. $^1$HNMR (CDCl$_3$) δ6.70 (m, 0.4H), 6.18 (m, 0.6H), 4.47 (m, 1H), δ3.1–0.8 (a series of complex m, 16H). BP 105°–162° C. at 0.20 mm Hg. Yield 52%

EXAMPLE XIX

The process of Example I was repeated except that the aldehyde was butanal to obtain 3-butylenedihydro-5-methyl-2 (3H)-furanone. $^1$HNMR (CDCl$_3$) δ6.70 (m, 0.6H), δ6.19 (m, 0.4H), 4.65 (m, 1H), 3.04 (M, 1H), 2.75–2.00 (series of m, 3H), 1.47 (m, 5H), δ0.95 (d of t, 3H) BP 92°–105° C. at 0.65 mm Hg. Yield 58%

EXAMPLE XX

To a mixture of 14.9 gms (0.100 mole) of 3-acetyldihydro-5-methyl-2(3H)-furanone in 100 ml of propionaldehyde diethyl acetal was charged 4.00 g (0.100 mole) of sodium hydroxide. The reaction vessel was a 250 mL flask fitted with a mechanical stirrer and Dean-Stark water trap. The mixture was heated under reflux for 5.5 hours. Afterwards 14.0 g (0.125 mole) of cyclohexanecarboxaldehyde was added over a 1-hour period. The mixture was heated under reflux for an additional 12 hours and was then worked up as in Example I. The result was 19 grams of an oil containing 37% of Z-3-cyclohexylmethylene-5-methyl-dihydro-2(3H)-furanone and 24% of the E-isomer (GLC-raw area data).

I claim:

1. A process for the stereoselective synthesis of a 3-alkylidenedihydro-2(3H)-furanone of the formula

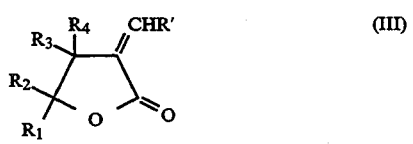
(III)

wherein $R^1$, $R^2$, $R^3$, $R^4$ are independently hydrogen or a hydrocarbon radical having from 1 to 20 carbon atoms and R' is a $C_{1-20}$ alkyl, alkenyl, cycloalkyl, or cycloalkenyl radical having a Taft Steric Substituent constant equal to or less than about −0.79, comprising the steps of:

A. reacting together
   (a) a 3-acyldihydro-2(3H)-furanone of the formula

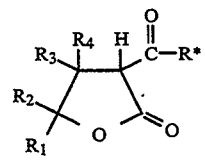
(I)

wherein $R^1$, $R^2$, $R^3$, $R^4$ have the meanings given above, and R* is a $C_{1-8}$ alkyl group,
   (b) an aldehyde of the formula R'CHO wherein R' has the meaning given above, and
   (c) an alkali metal hydroxide, at a temperature of from about 50° to about 150° in an inert diluent while removing water of reaction to form a reaction mixture containing at least the Z isomer of 3-alkylidenedihydro-2(3H)-furanone wherein when the E isomer is also present the Z/E mole ratio is greater than 1.0; and B. isolating at least the Z isomer from the reaction mixture.

2. The process of claim 1 wherein in step A components (a), (b) and (c) are present in substantially equimolar quantities.

3. The process of claim 1 wherein when both Z and E isomers are present in the reaction mixture from step A, the mixture of isomers is isolated from the reaction mixture, and at least the Z isomer is then isolated from the mixture of isomers in substantially pure form.

4. The process of claim 3 wherein both the E and the Z isomers are isolated from the mixture of isomers in substantially pure form.

5. The process of claim 1 wherein the inert diluent of step A forms an azeotrope with water boiling in the range of from about 50° C. to about 95° C. and is present at a volume ratio of diluent:total reactant charge of about 1:1 to about 20:1.

6. The process of claim 5 wherein the diluent is selected from the group consisting of benzene, toluene, xylene and cyclohexane and the volume ratio of diluent to reactants ranges from about 2:1 to about 8:1.

7. The process of claim 1 wherein the alkali metal hydroxide is sodium hydroxide.

8. The process of claim 1 wherein the hydrocarbon radicals $R^1$, $R^2$, $R^3$ and $R^4$ are selected from the group consisting of $C_{1-8}$ alkyl, $C_{3-6}$ cycloalkyl, phenyl, $C_{1-8}$ alkyl-substituted phenyl, benzyl and $C_{1-8}$ alkyl-substituted benzyl.

9. The process of claim 1 wherein R* is $C_{1-4}$ alkyl, $R_1$, $R_2$, $R_3$ and $R_4$ are hydrogen or $C_{1-8}$ alkyl and R' is hydrogen, $C_{1-8}$ alkyl or alkenyl, $C_{3-8}$ cycloalkyl or cycloalkenyl.

10. The process of claim 1 wherein in step A the α-acyl lactone and alkali metal hydroxide are combined and reacted prior to addition of the aldehyde.

11. The process of claim 10 wherein the aldehyde is added after about 60% to about 75% of the theoretical amount of water is removed.

12. The process of claim 1 wherein a molar excess of component (b) in step A is employed.

13. A process for the stereoselective synthesis of a 3-alkylidenedihydro-2(3H)-furanone of the formula

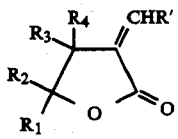

(III)

wherein $R^1$, $R^2$, $R^3$, $R^4$ are independently hydrogen or a hydrocarbon radical having from 1 to 20 carbon atoms and $R'$ is a $C_{1-20}$ alkyl, alkenyl, cycloalkyl or cycloalkenyl radical having a Taft Steric Substituent constant greater than about $-0.79$, comprising the steps of:

A. reacting together
(a) a 3-acyldihydro-2(3H)-furanone of the formula

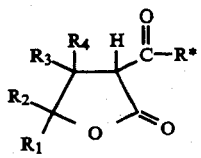

(I)

wherein $R^1$, $R^2$, $R^3$, $R^4$ have the meanings given above, and $R^*$ is a $C_{1-8}$ alkyl group,
(b) an aldehyde of the formula $R'CHO$ wherein $R'$ has the meaning given above, and
(c) an alkali metal hydroxide, at a temperature of from about 50° C. to about 150° C. in an inert diluent while removing water of reaction to form a reaction mixture containing at least the E isomer of 3-alkylidenedihydro-2(3H)-furanone wherein when the Z isomer is also present the E/Z mole ratio is greater than 1.0; and B. isolating at least the E isomer from the reaction mixture.

14. The process of claim 13 wherein in step A components (a), (b) and (c) are present in substantially equimolar quantities.

15. The process of claim 13 wherein when both Z and E isomers are present in the reaction mixture from step A, the mixture of isomers is isolated from the reaction mixture, and at least the E isomer is then isolated from the mixture of isomers in substantially pure form.

16. The process of claim 15 wherein both the E and the Z isomers are isolated from the mixture of isomers in substantially pure form.

17. The process of claim 13 wherein the inert diluent of step A forms an azeotrope with water boiling in the range of from about 50° C. to about 95° C. and is present at a volume ratio of diluent:total reactant charge of about 1:1 to about 20:1.

18. The process of claim 17 wherein the diluent is selected from the group consisting of benzene, toluene, xylene and cyclohexane and the volume ratio of diluent to reactants ranges from about 2:1 to about 8:1.

19. The process of claim 13 wherein the alkali metal hydroxide is sodium hydroxide.

20. The process of claim 13 wherein the hydrocarbon radicals $R_1$, $R_2$, $R_3$ and $R_4$ are selected from the group consisting of $C_{1-8}$ alkyl, $C_{3-6}$ cycloalkyl, phenyl, $C_{1-8}$ alkyl-substituted phenyl, benzyl and $C_{1-8}$ alkyl-substituted benzyl.

21. The process of claim 13 wherein $R^*$ is $C_{1-4}$ alkyl, $R_1$, $R_2$, $R_3$ and $R_4$ are hydrogen or $C_{1-8}$ alkyl and $R'$ is $C_{1-8}$ alkyl or alkenyl, or $C_{3-8}$ cycloalkyl or cycloalkenyl.

22. The process of claim 13 wherein in step A the α-acyl lactone and alkali metal hydroxide are combined and reacted prior to addition of the aldehyde.

23. The process of claim 22 wherein the aldehyde is added after about 60% to about 75% of the theoretical amount of water is removed.

24. The process of claim 13 wherein a molar excess of component (b) in step A is employed.

25. A process for the stereoselective synthesis of an α-alkylidene-δ-valerolactone of the formula

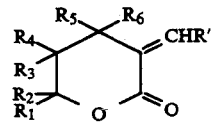

(IV)

wherein $R_1$, $R_2$, $R_3$, $R_4$, $R_5$ and $R_6$ are independently hydrogen or a hydrocarbon radical having from 1 to 20 carbon atoms and $R'$ is a $C_{1-20}$ alkyl, alkenyl, cycloalkyl or cycloalkenyl radical having a Taft Steric Substituent constant equal to or less than about $-0.79$, comprising the steps of:

A. reacting together
(a) an acyl lactone of the formula

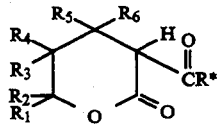

(II)

wherein $R_1$, $R_2$, $R_3$, $R_4$, $R_5$ and $R_6$ have the meanings given above, and $R^*$ is a $C_{1-8}$ alkyl group,
(b) an aldehyde of the formula $R'CHO$ wherein $R'$ has the meaning given above, and
(c) an alkali metal hydroxide, at a temperature of from about 50° C. to about 150° C. in an inert diluent while removing water of reaction to form a reaction mixture containing at least the Z isomer of the α-alkylidene-δ-valerolactone of formula IV wherein when the E isomer is also present the Z/E mole ratio is greater than 1.0; and B. isolating at least the Z isomer from the reaction mixture.

26. The process of claim 25 wherein in step A components (a), (b) and (c) are present in substantially equimolar quantities.

27. The process of claim 25 wherein when both Z and E isomers are present in the reaction mixture from step A, the mixture of isomers is isolated from the reaction mixture, and at least the Z isomer is then isolated from the mixture of isomers in substantially pure form.

28. The process of claim 27 wherein both the E and the Z isomers are isolated from the mixture of isomers in substantially pure form.

29. The process of claim 25 wherein the inert diluent of step A forms an azeotrope with water boiling in the range of from about 50° C. to about 95° C. and is present at a volume ratio of diluent:total reactant charge of about 1:1 to about 20:1.

30. The process of claim 29 wherein the diluent is selected from the group consisting of benzene, toluene, xylene and cyclohexane and the volume ratio of diluent to reactants ranges from about 2:1 to about 8:1.

31. The process of claim 25 wherein the alkali metal hydroxide is sodium hydroxide.

32. The process of claim 25 wherein the hydrocarbon radicals $R_1$, $R_2$, $R_3$, $R_4$, $R_5$ and $R_6$ are selected from the group consisting of $C_{1-8}$ alkyl, $C_{3-6}$ cycloalkyl, phenyl, $C_{1-8}$ alkyl-substituted phenyl, benzyl and $C_{1-8}$ alkyl-substituted benzyl.

33. The process of claim 25 wherein $R^*$ is $C_{1-4}$ alkyl, $R_1$, $R_2$, $R_3$, $R_4$, $R_5$ and $R_6$ are hydrogen or $C_{1-8}$ alkyl and $R'$ is $C_{1-8}$ alkyl or alkenyl, or $C_{3-8}$ cycloalkyl or cycloalkenyl.

34. The process of claim 25 wherein in step A the $\alpha$-acyl lactone and alkali metal hydroxide are combined and reacted prior to addition of the aldehyde.

35. The process of claim 34 wherein the aldehyde is added after about 60% to above 75% of the theoretical amount of water is removed.

36. The process of claim 25 wherein a molar excess of component (b) in step A is employed.

37. A process for the stereoselective synthesis of an $\alpha$-alkylidene-$\delta$-valerolactone of the formula

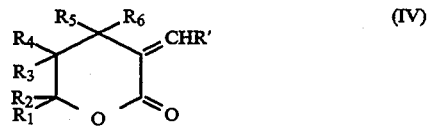

wherein $R_1$, $R_2$, $R_3$, $R_4$, $R_5$ and $R_6$ are independently hydrogen or a hydrocarbon radical having from 1 to 20 carbon atoms and $R'$ is a $C_{1-20}$ alkyl, alkenyl, cycloalkyl or cycloalkenyl radical having a Taft Steric Substituent constant greater than about $-0.79$, comprising the steps of:

A. reacting together
(a) an acyl lactone of the formula

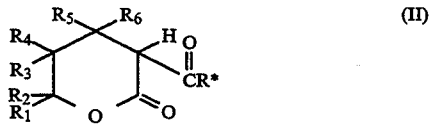

wherein $R_1$, $R_2$, $R_3$, $R_4$, $R_5$ and $R_6$ have the meanings given above, and $R^*$ is a $C_{1-8}$ alkyl group,
(b) an aldehyde of the formula $R'CHO$ wherein $R'$ has the meaning given above, and
(c) an alkali metal hydroxide, at a temperature of from about 50° C. to about 150° C. in an inert diluent while removing water of reaction to form a reaction mixture containing at least the E isomer of the $\alpha$-alkylidene-$\delta$-valerolactone of formula IV wherein when the Z isomer is also present the E/Z mole ratio is greater than 1.0; and B. isolating at least the E isomer from the reaction mixture.

38. The process of claim 37 wherein in step A components (a), (b) and (c) are present in substantially equimolar quantities.

39. The process of claim 37 wherein when both Z and E isomers are present in the reaction mixture from step A, the mixture of isomers is isolated from the reaction mixture, and at least the E isomer is then isolated from the mixture of isomers in substantially pure form.

40. The process of claim 39 wherein both the E and the Z isomers are isolated from the mixture of isomers in substantially pure form.

41. The process of claim 37 wherein the inert diluent of step A forms an azeotrope with water boiling in the range of from about 50° C. to about 95° C. and is present at a volume ratio of diluent:total reactant charge of about 1:1 to about 20:1.

42. The process of claim 41 wherein the diluent is selected from the group consisting of benzene, toluene, xylene and cyclohexane and the volume ratio of diluent to reactants ranges from about 2:1 to about 8:1.

43. The process of claim 37 wherein the alkali metal hydroxide is sodium hydroxide.

44. The process of claim 37 wherein the hydrocarbon radicals $R_1$, $R_2$, $R_3$, $R_4$, $R_5$ and $R_6$ are selected from the group consisting of $C_{1-8}$ alkyl, $C_{3-6}$ cycloalkyl, phenyl, $C_{1-8}$ alkyl-substituted phenyl, benzyl and $C_{1-8}$ alkyl-substituted benzyl.

45. The process of claim 37 wherein $R^*$ is $C_{1-4}$ alkyl, $R_1$, $R_2$, $R_3$, $R_4$, $R_5$ and $R_6$ are hydrogen or $C_{1-8}$ alkyl and $R'$ is $C_{1-8}$ alkyl or alkenyl, or $C_{3-8}$ cycloalkyl or cycloalkenyl.

46. The process of claim 37 wherein in step A the $\alpha$-acyl lactone and alkali metal hydroxide are combined and reacted prior to addition of the aldehyde.

47. The process of claim 46 wherein the aldehyde is added after about 60% to about 75% of the theoretical amount of water is removed.

48. The process of claim 37 wherein a molar excess of component (b) in step A is employed.

* * * * *

UNITED STATES PATENT AND TRADEMARK OFFICE
CERTIFICATE OF CORRECTION

PATENT NO. : 5,416,224
DATED : May 16, 1995
INVENTOR(S) : Louis Rebrovic

It is certified that error appears in the above-indentified patent and that said Letters Patent is hereby corrected as shown below:

In col. 1, line 40, delete [s-position] and insert --α-position--.

In col. 5, lines 41-42, delete [s-acetyl] and insert --α-acetyl--.

In col. 7, line 52, delete [21,775] and insert --21.775--.

In col. 8, line 7, delete [66.55] and insert --6.55--.

In col. 8, line 41, delete [121,712] and insert --121.712-- and delete [35,979] and insert --35.979--.

In col. 8, line 42, delete [33,550] and insert --33.550--, delete [22,414] and insert --22.414--, and delete [13,919] and insert --13.919--.

Signed and Sealed this

Tenth Day of September, 1996

Attest:

BRUCE LEHMAN

*Attesting Officer*     *Commissioner of Patents and Trademarks*